United States Patent
Malisz et al.

(10) Patent No.: US 11,904,279 B2
(45) Date of Patent: Feb. 20, 2024

(54) REMOVAL OF AL-SALTS, HCL, NACL AND ORGANIC BY-PRODUCT FROM STRONG ALKALINE DIOPAT SUSPENSION BY MEANS OF ALKALINE STABLE NANOFILTRATION FOLLOWED BY SEPARATION OF SALTS AND BYPRODUCTS AFTER NEUTRALIZATION OF DIOPAT SOLUTION BY MEANS OF ULTRAFILTRATION

(71) Applicant: BASF SE, Ludwigshafen am Rhein (DE)

(72) Inventors: Jacek Malisz, Ludwigshafen am Rhein (DE); Johannes Nagel, Ludwigshafen am Rhein (DE); Michael Jacquier, Binzen (DE)

(73) Assignee: BASF SE, Ludwigshafen am Rhein (DE)

( * ) Notice: Subject to any disclaimer, the term of this patent is extended or adjusted under 35 U.S.C. 154(b) by 337 days.

(21) Appl. No.: 17/290,698

(22) PCT Filed: Oct. 30, 2019

(86) PCT No.: PCT/EP2019/079711
§ 371 (c)(1),
(2) Date: Apr. 30, 2021

(87) PCT Pub. No.: WO2020/089323
PCT Pub. Date: May 7, 2020

(65) Prior Publication Data
US 2022/0016576 A1  Jan. 20, 2022

(30) Foreign Application Priority Data
Oct. 30, 2018  (EP) ..................... 18203387

(51) Int. Cl.
*B01D 61/02* (2006.01)
*B01D 61/58* (2006.01)
*B01D 71/02* (2006.01)
*C07D 251/24* (2006.01)
*B01D 61/14* (2006.01)
*B01D 71/68* (2006.01)

(52) U.S. Cl.
CPC ........... *B01D 61/58* (2013.01); *B01D 61/027* (2013.01); *B01D 61/145* (2013.01); *B01D 71/025* (2013.01); *C07D 251/24* (2013.01); *B01D 71/68* (2013.01); *B01D 2311/08* (2013.01); *B01D 2311/10* (2013.01); *B01D 2311/14* (2013.01); *B01D 2311/18* (2013.01); *B01D 2311/2642* (2013.01); *B01D 2311/2649* (2013.01)

(58) Field of Classification Search
CPC ..... B01D 61/027; B01D 61/58; C07D 251/24
See application file for complete search history.

(56) References Cited

U.S. PATENT DOCUMENTS

| | | | |
|---|---|---|---|
| 3,118,887 A | 1/1964 | Hardy et al. | |
| 2013/0048564 A1 | 2/2013 | Stewart et al. | |
| 2015/0217240 A1* | 8/2015 | Van Tuel ............ | B01D 69/148 427/244 |

FOREIGN PATENT DOCUMENTS

| | | |
|---|---|---|
| CN | 101429345 A | 5/2009 |
| CN | 101654894 A | 2/2010 |
| CN | 102477227 A | 5/2012 |
| CN | 102992515 A | 3/2013 |
| EP | 0197006 A2 * | 10/1986 |
| WO | 2004/024828 A1 | 3/2004 |

OTHER PUBLICATIONS

Fortsch Bruno et al—EP-0197006-A2 machine translation (Year: 1986).*
International Preliminary Report on Patentability received for PCT Patent Application No. PCT/EP2019/079711, dated May 14, 2021, 8 pages.
International Search Report and Written Opinion received for PCT Patent Application No. PCT/EP2019/079711, dated Jan. 23, 2020, 14 pages.
Rakhshan et al., "The effect of functionalized Sio2nanoparticles on the morphology and triazines separation properties of cellulose acetate membranes", Journal of Industrial and Engineering Chemistry, vol. 34, Oct. 29, 2015, pp. 51-60.

* cited by examiner

*Primary Examiner* — Bradley R Spies
(74) *Attorney, Agent, or Firm* — Faegre Drinker Biddle & Reath LLP

(57) ABSTRACT

The present invention provides an improved process for isolating 2,4-bis-(2,4-dihydroxyphenyl)-6-(4-methoxyphenyl)-1,3,5-triazine (DIOPAT) from an aqueous alkaline mixture M having a pH of 10 or more and comprising the 2,4-bis-(2,4-dihydroxyphenyl)-6-(4-methoxyphenyl)-1,3,5-triazine, 2,4-dihydroxybenzophenone, and aluminum salts, wherein the process comprises a nanofiltration step, a precipitation step, and a further filtration step.

19 Claims, No Drawings

REMOVAL OF AL-SALTS, HCL, NACL AND ORGANIC BY-PRODUCT FROM STRONG ALKALINE DIOPAT SUSPENSION BY MEANS OF ALKALINE STABLE NANOFILTRATION FOLLOWED BY SEPARATION OF SALTS AND BYPRODUCTS AFTER NEUTRALIZATION OF DIOPAT SOLUTION BY MEANS OF ULTRAFILTRATION

CROSS-REFERENCE TO RELATED APPLICATIONS

This application is a national stage application (under 35 U.S.C. § 371) of PCT/EP2019/079711, filed Oct. 30, 2019, which claims benefit of European Application No. 18203387.8, filed Oct. 30, 2018, both of which are incorporated herein by reference in their entirety.

The present invention provides an improved process for isolating 2,4-bis-(2,4-dihydroxyphenyl)-6-(4-methoxyphenyl)-1,3,5-triazine (DIOPAT) from an aqueous alkaline mixture M having a pH of 10 or more and comprising the 2,4-bis-(2,4-dihydroxyphenyl)-6-(4-methoxyphenyl)-1,3,5-triazine, 2,4-dihydroxybenzophenone, and aluminum salts, wherein the process comprises the steps of separating the 2,4-bis-(2,4-dihydroxyphenyl)-6-(4-methoxyphenyl)-1,3,5-triazine from the aluminum salts and the 2,4-dihydroxybenzophenone by nanofiltration of the alkaline mixture M, wherein the 2,4-bis-(2,4-dihydroxyphenyl)-6-(4-methoxyphenyl)-1,3,5-triazine is obtained in the form of an alkaline aqueous solution S as the retentate; precipitating the 2,4-bis-(2,4-dihydroxyphenyl)-6-(4-methoxyphenyl)-1,3,5-triazine by modifying the pH of the aqueous solution S to a value of 9.5 or lower; and separating the precipitated 2,4-bis-(2,4-dihydroxyphenyl)-6-(4-methoxyphenyl)-1,3,5-triazine from the aqueous solution S by filtration, wherein the 2,4-bis-(2,4-dihydroxyphenyl)-6-(4-methoxyphenyl)-1,3,5-triazine is obtained in the form of an aqueous suspension SP as the retentate.

2,4-bis-(2,4-dihydroxyphenyl)-6-(4-methoxyphenyl)-1,3,5-triazine (DIOPAT) is the starting material for the preparation of the UV absorber Tinosorb® S (also known as 2,2'-[6-(4-methoxyphenyl)-1,3,5-triazine-2,4-diyl] bis{5-[(2-ethylhexyl)oxy]phenol}, anisotriazine, bis-ethylhexyloxyphenol methoxyphenyl triazine, or bemotrizinol; CAS Number 187393-00-6) having the following chemical formula.

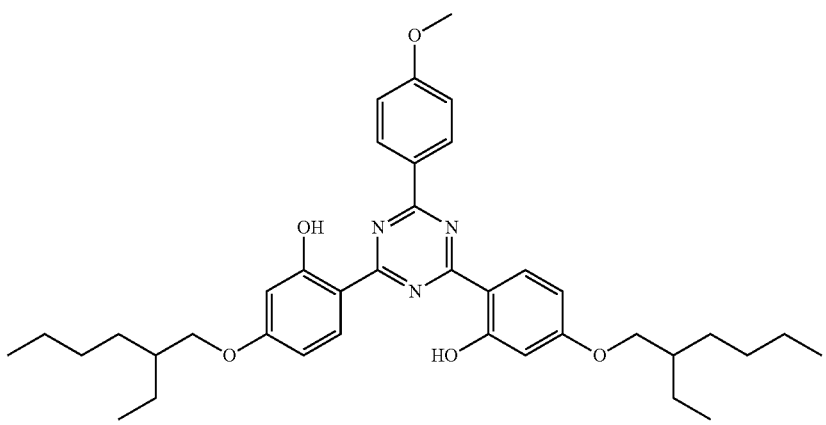

Tirosorb S

Tinosorb® S is a broad band UV absorber, absorbing UVB as well as UVA rays. Thus, Tinosorb® S is an important ingredient for sunscreen compositions and cosmetic applications.

One possible synthesis route to DIOPAT is performed via two steps, starting from 4-bromoanisole and cyanuric chloride under Grignard conditions to form the intermediate DICAT. In the second synthesis step, DICAT is reacted with resorcinol in a Friedel-Crafts reaction to form DIOPAT. In the following, the synthesis route to DIOPAT, starting from 4-bromoanisole and cyanuric chloride, is depicted, wherein the parameters a) Mg, THF, 65° C.; b) cyanuric chloride, THF, 0-5° C.; and c) resorcinol, toluene/benzonitrile, 45° C., AlCl$_3$ are typically applied.

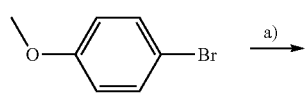

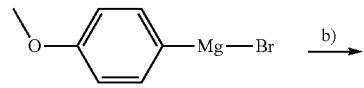

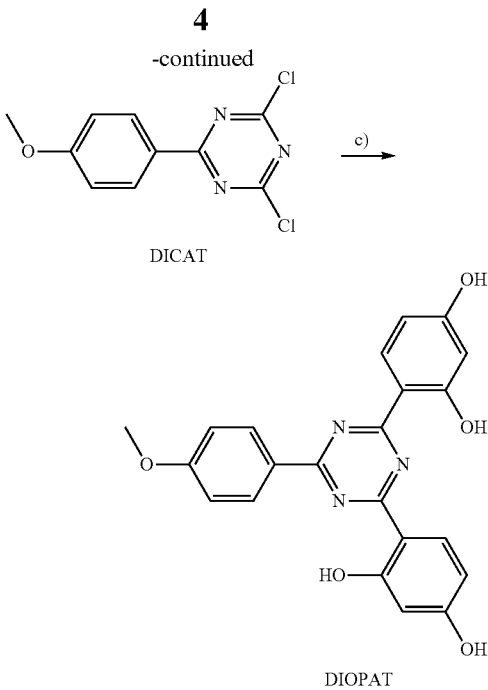

DICAT

DIOPAT

To complete the syntheses to Tinosorb® S, a third step, the alkylation of DIOPAT with isooctyl chloride, is performed. In the following, the reaction to Tinosorb® S is depicted, wherein the parameters a) isooctyl chloride, base, DMF, 143° C. are typically applied.

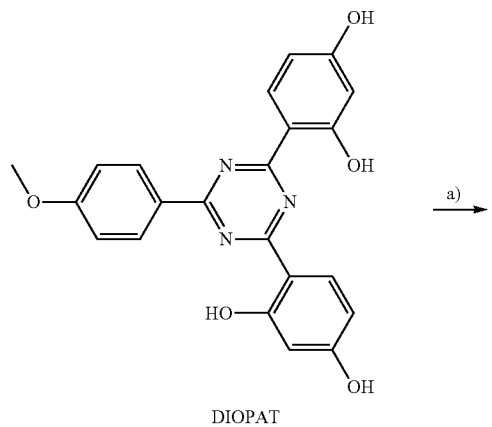

DIOPAT

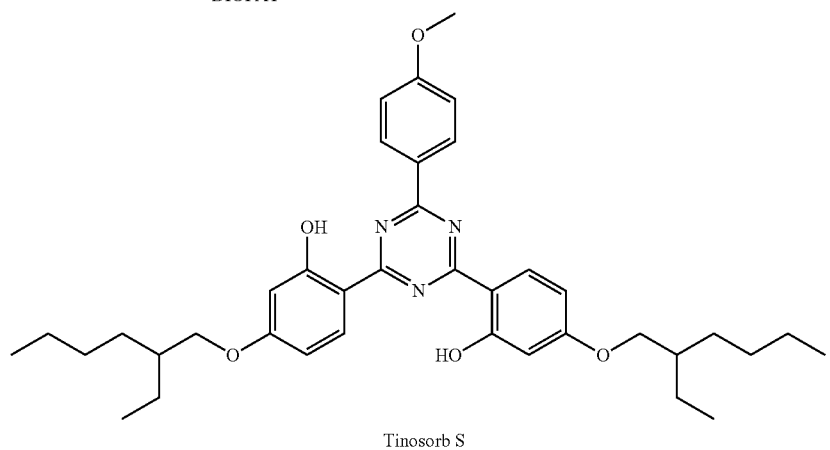

Tinosorb S

In connection with the preparation of DIOPAT, the workup procedure and isolation of DIOPAT causes difficulties.

Typically, the reaction mixture comprising DIOPAT is quenched on a pre-charged sodium hydroxide solution. The product DIOPAT as well as the aluminum salts (Al-salts) from the Friedel-Crafts reaction are then dissolved in the alkaline aqueous sodium hydroxide solution. The organic reaction solvent (e.g. a mixture of toluene and benzonitrile) is separated by phase separation. Residual organic solvents may be stripped off to guarantee an organic solvent free aqueous phase. Then, the DIOPAT is precipitated from the alkaline DIOPAT/Al-salt solution by acidifying the mixture. If a low pH is established (pH<1), the Al-salts are still dissolved in the aqueous phase while the DIOPAT is precipitated as a solid.

However, standard filtration processes, such as the use of a filter press, to separate the precipitated DIOPAT from the Al-salt solution have disadvantages. In particular, the filtration process is a manual, time consuming and open process, which is economically unattractive and causes safety issues on technical scale. Furthermore, the DIOPAT will be obtained together with the undesired organic impurity 2,4-dihydroxybenzophenone (2,4-DHBP), which is a byproduct of the DIOPAT preparation. Impurities of the undesired by-product of 2,4-DHBP in the DIOPAT, which is used for the final reaction step to Tinosorb® S, elevates the consumption of the expensive reactant isooctyl chloride and results in undesired side products, thus increasing the production costs.

An improved separation of the Al-salts from DIOPAT is challenging. Due to the low solubility of DIOPAT in organic solvents that have a complete miscibility gap between the aqueous and the organic phase, a separation of the Al-salts from DIOPAT by phase separation is not suitable. On the other hand, due to the corrosive behavior of acidic $AlCl_3$/DIOPAT suspensions, most filtration equipment where metallic material is in contact with these suspensions is not suitable. However, the Al-salts, as well as organic by-products, obtained in the Friedel-Crafts reaction with $AlCl_3$ are unfavorable for the following reaction to the final Tinosorb® S and need to be separated from DIOPAT.

Therefore, it was the object of the present invention to provide an improved process for isolating DIOPAT from the DIOPAT/Al-salt solution obtained after quenching the reaction mixture of the Friedel-Crafts reaction for preparing DIOPAT and removing the organic solvents.

It is a further object of the present invention to provide a process for isolating DIOPAT, which avoids a manual, time consuming and open filtration process.

It is another object of the present invention to provide an improved process for isolating DIOPAT, wherein not only aluminum salts but also organic by-products are simultaneously separated from the DIOPAT.

It has surprisingly been found that at least one of these objects can be achieved by a process for isolating 2,4-bis-(2,4-dihydroxyphenyl)-6-(4-methoxyphenyl)-1,3,5-triazine (DIOPAT) from an aqueous alkaline mixture M having a pH of 10 or more and comprising
  (i) the 2,4-bis-(2,4-dihydroxyphenyl)-6-(4-methoxyphenyl)-1,3,5-triazine;
  (ii) 2,4-dihydroxybenzophenone;
  (iii) aluminum salts;
  wherein the process comprises the steps of
  a) separating the 2,4-bis-(2,4-dihydroxyphenyl)-6-(4-methoxyphenyl)-1,3,5-triazine from the aluminum salts and the 2,4-dihydroxybenzophenone by nanofiltration of the alkaline mixture M, wherein the 2,4-bis-(2,4-dihydroxyphenyl)-6-(4-methoxyphenyl)-1,3,5-triazine is obtained in the form of an alkaline aqueous solution S as the retentate;
  b) precipitating the 2,4-bis-(2,4-dihydroxyphenyl)-6-(4-methoxyphenyl)-1,3,5-triazine by modifying the pH of the aqueous solution S to a value of 9.5 or lower;
  c) separating the precipitated 2,4-bis-(2,4-dihydroxyphenyl)-6-(4-methoxyphenyl)-1,3,5-triazine from the aqueous solution S by filtration, wherein the 2,4-bis-(2,4-dihydroxyphenyl)-6-(4-methoxyphenyl)-1,3,5-triazine is obtained in the form of an aqueous suspension SP as the retentate.

In particular, the present invention relates to a process for isolating 2,4-bis-(2,4-dihydroxyphenyl)-6-(4-methoxyphenyl)-1,3,5-triazine (DIOPAT) from an aqueous alkaline mixture M having a pH of 10 or more and comprising
  (i) the 2,4-bis-(2,4-dihydroxyphenyl)-6-(4-methoxyphenyl)-1,3,5-triazine;
  (ii) 2,4-dihydroxybenzophenone;
  (iii) aluminum salts;
  wherein the process comprises the steps of
  a) separating the 2,4-bis-(2,4-dihydroxyphenyl)-6-(4-methoxyphenyl)-1,3,5-triazine from the aluminum salts and the 2,4-dihydroxybenzophenone by nanofiltration of the alkaline mixture M, wherein the 2,4-bis-(2,4-dihydroxyphenyl)-6-(4-methoxyphenyl)-1,3,5-triazine is obtained in the form of an alkaline aqueous solution S as the retentate;
  b) precipitating the 2,4-bis-(2,4-dihydroxyphenyl)-6-(4-methoxyphenyl)-1,3,5-triazine by modifying the pH of the aqueous solution S to a value of 9.5 or lower;
  c) separating the precipitated 2,4-bis-(2,4-dihydroxyphenyl)-6-(4-methoxyphenyl)-1,3,5-triazine from the aqueous solution S by filtration, wherein the 2,4-bis-(2,4-dihydroxyphenyl)-6-(4-methoxyphenyl)-1,3,5-triazine is obtained in the form of an aqueous suspension SP as the retentate;
  wherein the nanofiltration step a) is performed at a pressure of from 10 to 30 bar and at a temperature in the range of from 20 to 60° C.

In one embodiment of the invention, the nanofiltration step a) is performed with a nanofiltration membrane having a sodium chloride retention rate of at least 60%, preferably from 60% to 75%. The sodium chloride retention rate is measured at 25° C. at 10 bar with a starting concentration of sodium chloride of 500 ppm and with 10-15% permeate yield.

As indicated above, the main purpose of the process of the present invention is the removal of Al-salts from the aqueous alkaline mixture M comprising DIOPAT, wherein said mixture is obtained after the Friedel-Crafts reaction, quenching and removal of the organic phase. This object can advantageously be achieved according to the present invention by performing first a nanofiltration step with the alkaline mixture. It was a surprising finding that in spite of the low molar mass of DIOPAT, the DIOPAT is maintained nearly quantitatively in the retentate of the nanofiltration, while the aluminates and the 2,4-dihydroxybenzophenone and optionally further organic impurities are only maintained to a very low extent, and will thus mainly be found in the permeate of the nanofiltration. Without being bound to theory, the advantageous separation by nanofiltration according to the present invention may be explained by the fact that the DIOPAT is present in ionic form at the alkaline pH value. In particular, the DIOPAT may even be present in deprotonated form at all four hydroxy groups of the phenyl rings, so that a tetraanion is formed. As the nanofiltration membrane is preferably anionic itself, the transport of DIOPAT through the membrane is hindered. In contrast, the remaining compounds, which are present either in neutral or monoanionic form, can more easily pass the membrane.

Contrary to the process typically used in the art, acidifying the mixture to a pH of <1, in order to precipitate DIOPAT, while providing aluminum salts in dissolved form, is avoided. Instead, DIOPAT may remain in dissolved form, and separation of the DIOPAT from the aluminum salts and the 2,4-dihydroxybenzophenone is performed by nanofiltration based on the different molecular sizes and/or ionic charges of the molecules. In this context, it is a surprising finding of the present invention that, while the larger and negatively charged DIOPAT molecules will be retained by the membrane, the smaller 2,4-dihydroxybenzophenone can pass the membrane together with the ions of the aluminum salts, so that separation of the DIOPAT from these components is easily possible, whereby the DIOAT is typically obtained in the form of an alkaline aqueous solution S as the retentate. In a further step, the DIOPAT can then easily be precipitated from said alkaline aqueous solution S by modifying the pH to a value of 9.5 or lower, again avoiding a strong acidic pH value. Isolation of the precipitated DIOPAT from the aqueous solution S can then easily be achieved by filtration.

Preferred embodiments of the present invention can be found in the claims, the description and the examples. It is to be understood that the features mentioned above and those still to be illustrated below of the subject matter of the invention are preferred not only in the respective given combination but also in other combinations without leaving the scope of the invention.

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the term "about" or "approx." (approximately) denotes an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising". As used herein, the term "aqueous alkaline mixture M" refers to a mixture comprising components (i), (ii), and (iii) as defined herein, which is typically obtained after quenching the Friedel-Crafts reaction mixture to prepare DIOPAT, i.e. component (i), with an aqueous sodium hydroxide solution and removing the organic phase. The pH of the aqueous alkaline mixture M is 10 or more, and is preferably in a range of from 10 to 15, more preferably from 12 to 14, in particular from 12 to 13.5. The amount of Al-salts will typically be in the range of from 1 to 20% by weight, preferably from 1 to 10% by weight based on the total weight of the aqueous alkaline mixture M, and the amount of 2,4-DHBP will typically be in the range of from 0.5 to 5% by weight, preferably from 0.5 to 2% by weight based on the total weight of the aqueous alkaline mixture M. On the other hand, the amount of DIOPAT will typically be in the range of from 6 to 20% by weight, preferably from 7 to 14% by weight, based on the total weight of the aqueous alkaline mixture M.

As used herein "2,4-bis-(2,4-dihydroxyphenyl)-6-(4-methoxyphenyl)-1,3,5-triazine" (DIOPAT) is the compound of interest in the process of the present invention, as it is the precursor for the preparation of Tinosorb® S, as explained above. 2,4-dihydroxybenzophenone (2,4-DHBP) is a by-product of its preparation. As used herein, the term "aluminum salts" (Al-salts) refers to aluminum salts including aluminum trichloride and/or aluminum hydroxide as well as sodium aluminum oxide ($NaAlO_2$). These aluminum salts are obtained in the preparation of DIOPAT as aluminum trichloride is required for the Friedel-Crafts reaction.

It is to be understood that the aqueous alkaline mixture M may also comprise further components, e.g. sodium chloride, as a result of the reaction of aluminum trichloride with sodium hydroxide upon quenching, as well as sodium hydroxide. In addition, sodium aluminum oxide ($NaAlO_2$) may be formed upon quenching and therefore be present in the aqueous alkaline mixture M. Furthermore, residual amounts of the starting materials DICAT and resorcinol may be present, if the conversion to DIOPAT was incomplete or an excess of DICAT or resorcinol was used.

After the separation step a) of the process of the invention by nanofiltration, DIOPAT is obtained in the form of an alkaline solution S as the retentate.

As used herein, the term "aqueous solution S" refers to the solution obtained in step a) comprising DIOPAT. When obtained in step a), the aqueous solution S typically has a pH value of 10 or more, preferably from 10 to 15, more preferably from 12 to 14, in particular from 12 to 13.5, and is therefore referred to as "alkaline aqueous solution 5". It is to be understood that the alkaline aqueous solution S may not only comprise DIOPAT, but also residual amounts of Al-salts and 2,4-DHBP, and optionally other impurities as mentioned above. However, the residual amounts of aluminum will typically be below 1% by weight, preferably below 0.5% by weight or even below 0.2% by weight based on the total weight of the alkaline aqueous solution S, and the residual amounts of 2,4-DHBP will typically be below 2% by weight, preferably below 0.8% by weight or even below 0.7% by weight based on the total weight of the alkaline solution, while the amount of DIOPAT will typically be at least 6% by weight, preferably at least 7% by weight, more preferably at least 8% by weight of the alkaline aqueous solution S.

In step b) of the process of the invention, the pH of the aqueous solution S is then modified to pH of 9.5 or lower in order to precipitate the DIOPAT. As used herein "modifying the pH to a pH of 9.5 or lower" is performed with an acid. Preferred acids include strong inorganic acids, such as sulfuric acid or hydrochloric acid. Preferably, "modifying the pH to a pH of 9.5 or lower" in step b) of the process of the invention is performed with hydrochloric acid, in particular an aqueous hydrogen chloride solution. Preferred concentrations of the hydrogen chloride solution are in the range of from 20 to 37%, preferably in the range of from 36 to 37%. Preferably, the pH is modified to a pH of 8 or lower, preferably to a value in the range of from 6 to 8. As a result of the pH modifying step b), additional sodium chloride may be formed by reaction of sodium hydroxide with hydrogen chloride. Thus, after step b), the aqueous solution S preferably comprises an additional amount of sodium chloride.

As used herein, the term "precipitating" refers to solids formation of a compound. According to the present invention, DIOPAT is precipitated from the aqueous solution S obtained in step a) by modifying the pH of the aqueous solution S to a value of 9.5 or lower in step b), whereby the solubility of DIOPAT is significantly reduced, so that a precipitate is formed. In contrast, residual amounts of Al-salts and 2,4-DHBP, and optionally other impurities including sodium chloride will remain in dissolved form. Thus, after step b), the DIOPAT has been precipitated from the aqueous solution S, so that the product of step b) may also be referred to as a suspension.

In step c) of the process of the invention, the precipitated DIOPAT can then be separated from the aqueous solution S comprising residual amounts of Al-salts and 2,4 DHBP, and optionally other impurities as indicated above, in particular sodium chloride, by filtration. The DIOPAT is then obtained in the form of an aqueous suspension SP as the retentate.

The difference between the separation steps a) and c) of the process of the invention is that in step a) a nanofiltration is performed, wherein the separation is based on the molecular size rather than the dissolved or non-dissolved state as in case of the filtration according to step c).

As used herein, "nanofiltration" is performed with a nanofiltration membrane having a pore size of 2 nm or lower. Such nanofiltration membrane are also referred to in the art as having a standard NaCl retention of 70%. As nanofiltration is performed with an alkaline mixture M according to the present invention, the nanofiltration membrane is preferably a polymer-based nanofiltration membrane, in particular a polyethersulfone membrane filter available, e.g., from Nitto Denko, which is stable in strong alkaline solutions even at elevated temperatures.

In one embodiment of the invention, the nanofiltration step a) is performed with a nanofiltration membrane having a sodium chloride retention rate of at least 60%, preferably from 60% to 75%. The sodium chloride retention rate is measured at 25° C. at 10 bar with a starting concentration of sodium chloride of 500 ppm and with 10-15% permeate yield. Preferably, the nanofiltration membrane is a polymer-based membrane.

In the nanofiltration step a), the DIOPAT is retained from the membrane and therefore obtained in the retentate of the nanofiltration in view of the higher molecular size and high anionic charge. In the filtration step c), the DIOPAT is retained from the membrane and therefore obtained in the retentate of the filtration in view of its precipitated state. As used herein, the term "retentate" refers to the solution or suspension comprising the components, which does not pass the membrane, while the term "permeate" refers to the solution, which passes the membrane and comprises those components, for which the membrane is permeable, i.e. which pass the membrane.

The filtration steps a) and c) may preferably be performed by continuously pumping the respective mixture, solution or suspension from a feed vessel to the membrane and from there back to the feed vessel. Additional solvent, preferably water may continuously be added to the retentate, and the permeate may continuously be removed. This results in washing the DIOPAT in the retentate. Preferred washing factors are in the range of from 2 to 6, preferably from 2 to 5. The term "washing factor" in this connection refers to the amount of water relative to the mixture, solution or suspension to be separated.

The filtration step c) may also involve concentrating the retentate. As used herein, the term "concentration factor" refers to the ratio of the starting volume of the suspension or solution comprising the precipitated compound and the dissolved components to the final volume of the suspension comprising the precipitated compound (retentate), after the dissolved components and parts of the solvent (permeate) have been removed during the diafiltration process. It is to be understood that the concentration factor of the additional solvent, which may be continuously added to the retentate, does not affect the concentration factor, as the same amount of additional solvent, which is continuously added to the retentate, will be continuously removed from the system by removing the permeate.

As used herein, the term "suspension" denotes a heterogeneous mixture comprising a solvent and a precipitate. For the diafiltration process, the particles of the precipitate must be larger than the pore size of the membrane.

As used herein, the term "dissolution" or "solution" denotes a homogeneous mixture comprising a solvent and dissolved components, for example ions of a salt.

Preferred embodiments regarding the process of the invention are described hereinafter.

As already indicated above, the present invention relates to a process for isolating 2,4-bis-(2,4-dihydroxyphenyl)-6-(4-methoxyphenyl)-1,3,5-triazine (DIOPAT) from an aqueous alkaline mixture M having a pH of 10 or more and comprising the 2,4-bis-(2,4-dihydroxyphenyl)-6-(4-methoxyphenyl)-1,3,5-triazine, 2,4-dihydroxybenzophenone, and aluminum salts, wherein the process comprises the steps of separating the 2,4-bis-(2,4-dihydroxyphenyl)-6-(4-methoxyphenyl)-1,3,5-triazine from the aluminum salts and the 2,4-dihydroxybenzophenone by nanofiltration of the alkaline mixture M, wherein the 2,4-bis-(2,4-dihydroxyphenyl)-6-(4-methoxyphenyl)-1,3,5-triazine is obtained in the form of an alkaline aqueous solution S as the retentate; precipitating the 2,4-bis-(2,4-dihydroxyphenyl)-6-(4-methoxyphenyl)-1,3,5-triazine by modifying the pH of the aqueous solution S to a value of 9.5 or lower; and separating the precipitated 2,4-bis-(2,4-dihydroxyphenyl)-6-(4-methoxyphenyl)-1,3,5-triazine from the aqueous solution S by filtration, wherein the 2,4-bis-(2,4-dihydroxyphenyl)-6-(4-methoxyphenyl)-1,3,5-triazine is obtained in the form of an aqueous suspension SP as the retentate.

In step a) of the process according to the present invention, the separation of the 2,4-bis-(2,4-dihydroxyphenyl)-6-(4-methoxyphenyl)-1,3,5-triazine (DIOPAT) from the aluminum salts and the 2,4-dihydroxybenzophenone is performed by nanofiltration. As explained above, the DIOPAT is obtained in the form of an alkaline aqueous solution S as the retentate.

In a preferred embodiment, the nanofiltration step results in a separation of the DIOPAT from the aluminum salts and the 2,4-dihydroxybenzophenone, such that at least 95% by weight, preferably at least 98%, more preferably at least 99.5% by weight of the total amount of the DIOPAT originally contained in the aqueous alkaline mixture M is retained by the membrane and therefore obtained as the retentate. In another preferred embodiment, the nanofiltration step results in a separation of the DIOPAT from the aluminum salts and the 2,4-dihydroxybenzophenone, such that at least 95% by weight, preferably at least 98% by weight, more preferably at least 99% by weight of the total amount of the aluminum originally contained in the aqueous alkaline mixture M passes the membrane and is therefore obtained in the permeate. In another preferred embodiment, the nanofiltration step results in a separation of the DIOPAT from the aluminum salts and the 2,4-dihydroxybenzophenone, such that at least 80% by weight, preferably at least 90% by weight, more preferably at least 92% by weight of the total amount of the 2,4-dihydroxybenzophenone originally contained in the aqueous alkaline mixture M passes the membrane and is therefore obtained in the permeate.

In other words, in a preferred embodiment of the process of the present invention, the retentate obtained in step a) in the form of the aqueous solution S preferably comprises at least 95% by weight, preferably at least 98%, more preferably at least 99.5% by weight of the total amount of the DIOPAT originally contained in the aqueous alkaline mixture M, and additionally below 5% by weight, preferably below 2% by weight, more preferably below 1% by weight of the total amount of aluminum originally contained in the aqueous alkaline mixture M, and additionally below 20% by weight, preferably below 10% by weight, more preferably below 8% by weight of the total amount of the 2,4-dihydroxybenzophenone originally contained in the aqueous alkaline mixture M.

Thus, the amounts of aluminum and 2,4-dihydroxybenzophenone can be significantly decreased by performing the separation step a). This is particularly surprising with regard to the 2,4-dihydroxybenzophenone, which is normally difficult to separate from DIOPAT.

In a preferred embodiment, the nanofiltration step a) is performed with a polymer-based nanofiltration membrane having a pore size of less than 2 nm. In a more preferred embodiment, the polymer-based nanofiltration membrane is a polyethersulfone membrane.

The pore size may also be determined based on the NaCl retention. In a preferred embodiment, the nanofiltration step a) is performed with a polymer-based nanofiltration membrane, preferably a polyethersulfone membrane having a standard NaCl retention of at least 60%, preferably 70%. In another preferred embodiment of the invention, the nanofiltration step a) is performed with a nanofiltration membrane having a sodium chloride retention rate of from 60% to 75%. The sodium chloride retention rate is measured at 25° C. at 10 bar with a starting concentration of sodium chloride of 500 ppm and with 10-15% permeate yield. Preferably, the nanofiltration membrane is a polymer-based membrane.

The nanofiltration step a) is preferably performed at a temperature in the range of from 20 to 60° C., preferably in the range of from 30 to 60° C., more preferably in the range of from 50 to 60° C. These temperatures are preferred in order to ensure a sufficiently low viscosity of the alkaline mixture M, and therefore a satisfying membrane capacity. Furthermore, temperatures in the range of from 50 to 60° C. are particularly preferred in order to improve the permeability of 2,4-DHBP through the membrane. However, in order to improve the stability of DIOPAT at these temperatures, it is preferred that the nanofiltration step a) is performed in a protective gas atmosphere and/or under the exclusion of light.

In a preferred embodiment, the nanofiltration step a) is therefore performed in a protective gas atmosphere and/or under the exclusion of light. Preferably, nitrogen may be used as protective gas.

In another preferred embodiment, the nanofiltration step a) is performed at a pressure of from 10 to 30 bar, preferably from 15 to 25 bar, and at a temperature in the range of from 20 to 60° C., preferably from 50 to 60° C.

In another preferred embodiment, the nanofiltration step a) is performed at a pressure of from 15 to 25 bar, and at a temperature in the range of from 50 to 60° C.

The nanofiltration step a) preferably also involves washing of the retentate with water, in order to improve the separation of the DIOPAT from 2,4-DHBP and aluminum salts, i.e. to increase the amounts of 2,4-DHBP and aluminum salts permeating through the membrane thereby increasing the purity of the DIOPAT in the retentate. Suitable washing factors are in the range of from 2 to 6, preferably 2 to 5.

In a preferred embodiment, the nanofiltration step a) involves washing of the retentate with water, wherein the amount (i.e. the volume) of washing water is preferably at least three times as high as the amount (i.e. the volume) of the alkaline mixture M.

Preferably, washing water is continuously introduced into the nanofiltration system on the retentate side, while the permeate is continuously removed. Furthermore, it is preferred to preheat the washing water, preferably to a temperature in the range of from 50 to 60° C.

In a preferred embodiment, the separation step a) therefore involves continuous washing of the solution S in the retentate with water, and removing of the permeate. Preferably, the overall volume of the retentate and the permeate is kept constant by removing the same volume of permeate as the volume of washing water that is introduced into the retentate.

In step b) of the process of the present invention, the DIOPAT is precipitated by modifying the pH of the aqueous solution S to a value of 9.5 or lower. Modifying the pH may be performed by any suitable organic or inorganic acid. Preferred are inorganic acids, such as hydrogen chloride, hydrogen bromide, hydrogen iodine, sulfuric acid, or nitric acid. In particular, hydrogen chloride is used. Preferably, the acid is in form of an aqueous solution.

In principle, step b) may be performed by addition of the aqueous solution S to an acid, preferably an acidic solution, or by addition of an acid, preferably an acidic solution, to the aqueous solution S. Preferably, step b) is performed by addition of the aqueous solution S to an acidic aqueous solution or by addition of an acidic aqueous solution to the aqueous solution S. Preferably, the acidic aqueous solution is preheated to a temperature of from 50 to 60° C.

Furthermore, it is preferred that the aqueous solution S is diluted with water before modifying the pH value. Preferably, the aqueous solution S is diluted with at least the same volume of water in comparison to the aqueous solution S obtained as retentate.

Preferably, modifying the pH in step b) is performed with hydrogen chloride, preferably with a hydrogen chloride solution. Particularly preferably, the aqueous solution S is diluted with an at least the same volume of water, and then the diluted aqueous solution S is added to an aqueous hydrogen chloride solution. It is especially preferred that the hydrogen chloride solution has a concentration of in the range of from 20 to 37%, preferably in the range of from 36 to 37%.

Thus, in a preferred embodiment of the process of the invention, in the precipitation step b), modifying the pH is performed with hydrogen chloride, preferably by diluting the aqueous solution S with water and then adding the diluted aqueous solution S to an aqueous hydrogen chloride solution. Preferably, the hydrogen chloride solution has a concentration of in the range of from 20 to 37%, preferably in the range of from 36 to 37%. Preferably the dilution of the aqueous solution S with water is performed with at least the same volume of water.

As indicated above, the pH of the aqueous solution S is modified to pH of 9.5 or lower. It has been found that DIOPAT precipitates at a pH of 9.5 or lower. In principal, also acidic pH values are suitable. However, by establishing a too acidic pH value, the amount of sodium chloride formed as a byproduct increases significantly and has to be separated from the DIOPAT afterwards.

In a preferred embodiment of the process of the invention, the precipitation step b) is therefore performed by modifying the pH of the aqueous solution S to a value of 8 or lower, preferably to a value in the range of from 6 to 8. Furthermore, a neutralization step would additionally be required at the end of the process of the invention.

It is to be understood that, after step b) of the process of the invention, the aqueous solution S preferably contains an additional amount of sodium chloride from the neutralization reaction of sodium hydroxide from and hydrogen chloride, provided that hydrogen chloride is used for modifying the pH in step b).

In step c) of the process of the invention, the precipitated DIOPAT is separated from the aqueous solution S by filtration, wherein the DIOPAT is obtained in the form of an aqueous suspension SP as the retentate.

It is to be understood that, in step c) of the process of the invention, DIOPAT can be further purified due to the separation from the aqueous solution S comprising residual amounts of Al-salts and 2,4-DHBP, as well as preferably sodium chloride formed in step b) of the process of the invention. In particular, the chloride salts can be easily separated to a large extent from the DIOPAT. Thus, "separating the precipitated DIOPAT from the aqueous solution S" according to step c) of the process preferably also refers to the separation of the precipitated DIOPAT from one or more of the remaining components in the aqueous solution S, in particular from the chloride salts contained in the aqueous solution S. While the precipitated DIOPAT will not pass the membrane and will therefore be obtained in the retentate of the filtration, other components of the aqueous solution S, in particular sodium chloride, and optionally also the residual amounts of Al-salts and 2,4-DHBP will pass the membrane.

In a preferred embodiment, the filtration step c) results in a separation of the DIOPAT from the remaining components in the aqueous solution S, such that at least 95% by weight, preferably at least 98%, more preferably at least 99.5% by weight of the total amount of the DIOPAT originally contained in the suspension formed from the aqueous solution S in step b) is retained by the membrane and therefore obtained as the retentate. In another preferred embodiment, the filtration step c) results in a separation of the DIOPAT from the chloride salts, such that at least 60% by weight, preferably at least 80% by weight, more preferably at least 90% by weight of the total amount of the chloride originally contained in the suspension formed from the aqueous solution S in step b) passes the membrane and is therefore obtained in the permeate.

In other words, in a preferred embodiment of the process of the present invention, the retentate obtained in step c) in the form of the aqueous suspension SP preferably comprises at least 95% by weight, preferably at least 98%, more preferably at least 99.5% by weight of the total amount of the DIOPAT originally contained in the suspension formed from the aqueous solution S in step b), and additionally below 40% by weight, preferably below 20% by weight, more preferably below 10% by weight of the total amount of chloride originally contained in the suspension formed from the aqueous solution S in step b).

Furthermore, the DIOPAT can be separated from residual amounts of aluminum salts and 2,4-DHBP. Regarding the separation from residual amounts of DHBP, it is particularly advantageous to perform the filtration step c) at higher temperatures in the range of from 80 to 95° C., preferably from 85 to 90° C.

In a preferred embodiment, the filtration step c) is performed with a membrane having a pore size in the range of from 10 to 800 nm or from 20 to 500 nm, preferably from 50 to 200 nm. These pore sizes ensure permeability for dissolved sodium chloride, aluminum salts as well as organic impurities such as 2,4-DHBP.

Preferably, the pore size of the ceramic membrane is provided as the mean pore size as determined by the bubble-rest described in American Society for Testing and Materials Standard (ASMT) Method F316. Alternatively, the pore size of the ceramic membranes may be defined by the molecular weight cut off, which is preferably in the range of from 1 kD to 150 kD.

Preferred membrane materials include ceramic materials in view of their high stability under high temperatures of up to 100° C. or more. In another preferred embodiment, the filtration step c) is therefore performed with a ceramic membrane, which is a $TiO_2$, $ZrO_2$, or $Al_2O_3$ membrane, preferably an $\alpha$-$Al_2O_3$ membrane.

The ceramic membrane may be provided in the form of a tubular, multi-channel or monolithic element, wherein a multi-channel element is preferred. Typically, the ceramic material has a multilayer structure with pore sizes ranging from larger pore sizes to smaller pore sizes, in order to provide, e.g. a macroporous support and a microporous top layer oriented to the retentate.

For example, a ceramic membrane having a pore size of 50 nm as the relevant value for the diafiltration step may comprise membrane layers with pore sizes of 400 nm, 200 nm, and 50 nm, wherein the smaller pore sizes will be on the side of the retentate. For the characterization of the ceramic membrane regarding the filtration properties, the smallest pore size oriented to the permeate is of relevance.

In a preferred embodiment, the ceramic membrane is an $\alpha$-$Al_2O_3$ membrane having a pore size of 50 nm with 400/200/50 nm membrane layers.

In one embodiment of the present invention, the ceramic membrane is a tubular ceramic membrane, through which the retentate flows, while the permeate stream exits the tubular ceramic membrane laterally through the ceramic membrane.

In another embodiment of the present invention, the ceramic membrane is a multi-channel element comprising several channels within the ceramic membrane material, e.g. from 7 to 211 channels, preferably from 7 to 37 channels, wherein the retentate flows through the channels, while the permeate stream exits the multi-channel element laterally through the ceramic membrane. In a particular embodiment of the present invention, suitable multi-channel elements comprise 7, 19, 37, 61, 85, or 211 channels, preferably 7 or 19 channels.

The length of the multi-channel element is preferably in a range of from 0.5 to 2 m, preferably from 0.5 to 1.5 m, more preferably from 1.0 to 1.5 m.

The inner diameter of the channels of the multi-channel element is preferably in the range of from 2 to 8 mm. The overall diameter of the multi-channel element is preferably in the range of from 25 to 80 mm, preferably from 25 to 41 mm, more preferably 25.4 or 41 mm.

Thus, in a preferred embodiment of the invention, the ceramic membrane is provided in the form of a multi-channel element having a length of from 0.5 to 1.5 m and an inner channel diameter of from 3 to 8 mm, preferably of 6 mm, wherein the multi-channel element preferably comprises from 7 to 19 channels. Particularly preferred is a multi-channel element having a length of from 1.0 to 1.5 m, an inner channel diameter of 6 mm, wherein the multi-channel element preferably comprises 7 or 19 channels. The overall diameter is then preferably from 25 or 41 mm.

The filter surface per element can be calculated from the length, the inner channel diameter and the number of channels of the element. In certain embodiments, the filter surface per element is from 0.02 to 3 m², preferably from 0.02 to 2 m², more preferably from 0.05 to 1.5 m², in particular from 0.1 to 0.6 m².

According to the invention, a single-channel element may have, e.g., a 1/6 or a 1/16 geometry. Thereby, the 1/6 geometry denotes that the element has one channel and an inner channel diameter of 6 mm. A 1/16 geometry thus denotes that the element has one channel and an inner diameter of 16 mm.

According to the invention, the multi-channel element may have, e.g., a 7/6 (i.e. the element has seven channels and an inner channel diameter of 6 mm), a 19/3.3, a 37/2, a 19/4, a 19/6, a 37/3.8, a 61/2.5, a 19/8, a 85/3.3, or a 211/2 geometry. In one preferred embodiment, the multi-channel element has a 7/6 or 19/6 geometry and 1.2 to 1.5 m length. Particularly preferred is a multi-channel element with a 19/6 geometry and 1.5 m length.

In one embodiment, the filtration step c) is performed at a pressure of from 1 to 4 bar, preferably from 2 to 3 bar, and at a temperature in the range of from 20 to 95° C., preferably from 85 to 90° C.

The filtration step c) preferably also involves washing of the retentate with water, in order to improve the separation of the DIOPAT from the remaining components of the aqueous solution S. Suitable washing factors are in the range of from 2 to 6, preferably 2 to 5.

In a preferred embodiment, the filtration step c) involves washing of the retentate with water, wherein the amount (i.e. the volume) of washing water is preferably at least two times as high as the amount (i.e. the volume) of the aqueous solution S.

Preferably, washing water is continuously introduced into the filtration system on the retentate side, while the permeate is continuously removed. Furthermore, it is preferred to preheat the washing water, preferably to a temperature in the range of from 50 to 90° C.

In a preferred embodiment, the separation step c) therefore involves continuous washing of the suspension in the retentate with water, and removing of the permeate.

In one preferred embodiment, the overall volume of the retentate and the permeate is kept constant by removing the same volume of permeate as the volume of washing water that is introduced into the retentate.

In another preferred embodiment, the separation step c) may be performed such that the concentration of the DIOPAT in the aqueous suspension SP obtained as the retentate will be higher than the concentration of the DIOPAT in the suspension before step c) is performed. Depending on the initial concentration of DIOPAT, the filtration step c) provides the aqueous suspension SP with a dry content of 2,4-bis-(2,4-dihydroxyphenyl)-6-(4-methoxyphenyl)-1,3,5-triazine in the range of from 2 to 10% by weight based on the total weight of the aqueous suspension SP. For example, the dry content of DIOPAT in the initial suspension may be in the range of from 3 to 5% by weight, while the concentration of DIOPAT in the retentate obtained in step c) may be in the range of from 5.5 to 7.5% by weight.

The process of the present invention may further comprise additional steps for concentrating the aqueous suspension SP obtained in step c) and for drying the resulting concentrate. Concentrating may be performed by any method known in the art such as evaporation or filtration, preferably filtration.

With regard to concentrating by filtration, any known filter may be used, such as a Dyno Filter (Bokela).

Therefore, in a preferred embodiment, the process further comprises the step of d) concentrating the aqueous suspension SP obtained in step c) by filtration.

In a more preferred embodiment, the process further comprises the step of f) drying the concentrate obtained in step d).

In summary, the process of the present invention comprising steps a), b), and c) provides the DIOPAT in precipitated form in the form of an aqueous suspension SP after step c) has been performed. The obtained aqueous suspension of DIOPAT is preferably concentrated in comparison to the alkaline mixture M. Furthermore, the DIOPAT has been separated to a large extent from the 2,4-DHBP and aluminum salts as well as additional salts, such as in particular sodium chloride. At the same time, the process of the present invention avoids working at strong acidic pH values. Therefore, a neutralization reaction at the end of the process can be avoided.

The process for isolation DIOPAT according to the present invention is especially advantageous in view of production costs, as due to unexpected removal of 2,4-DHBP from the DIOPAT suspension, the consumption of the expensive reactant isooctyl chloride in the last reaction step to Tinosorb® S is reduced significantly. This reduces the costs of the final synthesis step to Tinosorb® S as well as the costs of product workup of Tinosorb® S to reach the final specification.

The present invention is further illustrated by the following example.

EXAMPLE

Sampling: The sampling and the analysis were the same independent from the process step. After each step, samples of permeate and retentate were taken for:

Dry content (DC) and NaCl content
Al content
Total Organic Carbon (TOC, only permeates)
DIOPAT content and content of side products (AHRT, 2,4-DHBP, DMPRT)
DC was measured with DC scales, NaCl was measured by titration, TOC was measured with a TOC analyzer. DIOPAT and side products were determined via HPLC using
Agilent 1100
column material: EUROSPH ER 100-C18/5 Knauer
column length: 25 cm, column diameter: 4 mm
column temperature: 20° C.
injection volume: 5 µl
mobile phase: eluent A: 900 Deionat (2)+100 acetate buffer pH 4.65 (3)+0.2% TBAHS, eluent B: acetonitrile (1)+0.2% TBAHS
method: flow: 1.0 mL/min, pressure: max. 400 bar, stop time: 30 min
timetable:

| Time | % A | % B |
| --- | --- | --- |
| 5 min | 50% | 50% |
| 25 min | 0% | 100% |
| 30 min | 0% | 100% |

According to the present invention, the Al-salts as well as undesired organic by-products are separated from the DIOPAT by a process comprising a nanofiltration step, a precipitation step, and a further filtration step. Further details in this regard are provided hereinafter.

An alkaline mixture having a pH in the range of from 12.5 to 13.0 comprising 76 g/L DIOPAT, 6.6 g/L 2,4-DHBP, 121 g/L NaCl, 13.4 g/L Al-salts, 1.1 g/L resorcin, 4.8 g/L benzoic acid, and 77% by weight water was used in the process.

Nanofiltration:

The glass parts of the nanofiltration apparatus were covered with aluminum foil, in order to exclude UV light. The feed container was constantly flooded with nitrogen in order to remove oxygen.

1 part by volume of the alkaline mixture was diluted with 0.3 parts by volume water and heated to 50° C. in the nanofiltration apparatus. In the first nanofiltration step, the volume of the solution in the retentate is reduced from 1.3 volume parts to 1.0 volume parts. Then, 2 parts by volume of water are added, and the solution is again reduced to 0.7 volume parts by diafiltration. Then, the 0.7 volume parts of the solution are combined with 1.5 parts by volume of water and subjected to diafiltration.

Membrane: Polyether sulfone membrane NTR7470 available from Nitto Denko (2.5 inch spiral wound module with 46 mil spacer)

Operating parameters:

Temperature: 50° C.

Cross flow: to reach DP of around 0.7 bars along the module (about 1.6 m³/h)

Feed pressure: 30 bars

Result:

The density of the solution was reduced from 1.188 g/mL to 1.058 g/mL.

The ratio of NaCl to DC (dry content) was reduced from 35.4 to 0.1% by weight, i.e. reduction of about 98%.

The ratio of DIOPAT to DC was increased from 27.9 to 72.7% by weight.

The Al content in the solution was reduced from 10500 ppm to 660 ppm.

The 2,4-DHBP content in the solution was reduced by about 50%.

Neutralization:

0.9 parts by volume water and 0.02 parts by volume hydrochloric acid (32% in water) were provided in a mixing tumbler reactor and heated to 60° C. Then, 1 part by volume of the NF concentrate was slowly added within 30 minutes, so that a pH of about 7 was established. The resulting product suspension was then subjected to ultrafiltration.

Ultrafiltration:

1 part by volume of the neutralized product suspension was diluted with 3 parts by volume of water, then diafiltrated, and concentrated to 0.8 parts by volume.

Membrane:

Channel element: 6 mm channel, 1 m long

Membrane material: α-$Al_2O_3$

Nominal pore size: 50 nm with 400/200/50 membrane layers

Operating parameters:

Temperature: 88° C.

Cross flow: 3 m/s

Feed pressure: 2.5 bars

Process parameters:

Dilution factor of the start suspension only dead volume of the pump

Total concentration factor (CF) 1.2

Total diafiltration factor 3

Results:

The ratio of NaCl to DC was reduced from 22 to 1.1% by weight. The NaCl concentration was reduced from 1.4% by weight to 0.08% by weight.

The ratio of DIOPAT/DC was increased from 68 to 87% by weight.

The 2,4-DHBP content was reduced by about 50%.

The invention claimed is:

1. A process for isolating 2,4-bis-(2,4-dihydroxyphenyl)-6-(4-methoxyphenyl)-1,3,5-triazine (DIOPAT) from an aqueous alkaline mixture M having a pH of 10 or more and comprising
   (i) the 2,4-bis-(2,4-dihydroxyphenyl)-6-(4-methoxyphenyl)-1,3,5-triazine;
   (ii) 2,4-dihydroxybenzophenone;
   (iii) aluminum salts;
   wherein the process comprises the steps of
   a) separating the 2,4-bis-(2,4-dihydroxyphenyl)-6-(4-methoxyphenyl)-1,3,5-triazine from the aluminum salts and the 2,4-dihydroxybenzophenone by nanofiltration of the alkaline mixture M, wherein the 2,4-bis-(2,4-dihydroxyphenyl)-6-(4-methoxyphenyl)-1,3,5-triazine is obtained in the form of an alkaline aqueous solution S as the retentate;
   b) precipitating the 2,4-bis-(2,4-dihydroxyphenyl)-6-(4-methoxyphenyl)-1,3,5-triazine by modifying the pH of the aqueous solution S to a value of 9.5 or lower;
   c) separating the precipitated 2,4-bis-(2,4-dihydroxyphenyl)-6-(4-methoxyphenyl)-1,3,5-triazine from the aqueous solution S by filtration, wherein the 2,4-bis-(2,4-dihydroxyphenyl)-6-(4-methoxyphenyl)-1,3,5-triazine is obtained in the form of an aqueous suspension SP as the retentate;
   wherein the nanofiltration step a) is performed at a pressure of from 10 to 30 bar and at a temperature in the range of from 20 to 60° C.; and
   wherein the nanofiltration step a) is performed with a nanofiltration membrane having a sodium chloride retention rate of 60 to 75%, as measured at 25° C. and 10 bar at a starting concentration of sodium chloride of 500 ppm and with 10-15 permeate yield.

2. The process of claim 1, wherein the nanofiltration step a) is performed with a polymer-based nanofiltration membrane.

3. Process of claim 2, wherein the polymer-based nanofiltration membrane has a pore size of 2 nm or lower.

4. The process of claim 1, wherein the nanofiltration step a) is performed in a protective gas atmosphere and/or under the exclusion of light.

5. The process of claim 1, wherein the nanofiltration step a) is performed at a pressure of from 15 to 25 bar, and at a temperature in the range of from 50 to 60° C.

6. The process of claim 1, wherein the nanofiltration step a) involves washing of the retentate with water.

7. Process of claim 6, wherein the amount of washing water is at least three times as high as the amount of the alkaline mixture M.

8. The process of claim 1, wherein in the precipitation step b) modifying the pH is performed with hydrogen chloride.

9. Process of claim 8, wherein the in the precipitation step b) modifying the pH is performed by diluting the aqueous solution S with water and then adding the diluted aqueous solution S to an aqueous hydrogen chloride solution.

10. The process of claim 1, wherein the precipitation step b) is performed by modifying the pH of the aqueous solution S to a value of 8 or lower.

11. The process of claim 1, wherein the filtration step c) is performed with a membrane having a pore size in the range of from 20 to 500 nm.

12. The process of claim 1, wherein the filtration step c) is performed with a ceramic membrane, which is a $TiO_2$, $ZrO_2$, or $Al_2O_3$ membrane.

13. Process of claim 12, wherein the ceramic membrane is an $\alpha$-$Al_2O_3$ membrane.

14. The process of claim 1, wherein the filtration step c) is performed at a pressure of from 1 to 6 bar, and at a temperature in the range of from 20 to 95° C.

15. The process of claim 1, wherein the filtration step c) involves washing of the retentate with water.

16. Process of claim 15, wherein the amount of washing water is at least two times as high as the amount of the aqueous solution S.

17. The process of claim 1, wherein the filtration step c) provides the aqueous suspension SP with a dry content of 2,4-bis-(2,4-dihydroxyphenyl)-6-(4-methoxyphenyl)-1,3,5-triazine in the range of from 2 to 10% by weight based on the total weight of the aqueous suspension SP.

18. The process of claim 1, wherein the process further comprises the step of d) concentrating the aqueous suspension SP obtained in step c) by filtration.

19. The process of claim 18, wherein the process further comprises the step of e) drying the concentrate obtained in step d).

* * * * *